US005845003A

United States Patent [19]

[11] Patent Number: 5,845,003

[45] Date of Patent: Dec. 1, 1998

Hu et al.

[54] DETECTOR Z-AXIS GAIN CORRECTION FOR A CT SYSTEM

[75] Inventors: Hui Hu, Waukesha; Guy M. Besson, Franklin; David M. Hoffman, New Berlin, all of Wis.

[73] Assignee: General Electric Company, Milwaukee, Wis.

[21] Appl. No.: 879,684

[22] Filed: Jul. 8, 1997

Related U.S. Application Data

[63] Continuation of Ser. No. 376,813, Jan. 23, 1995, abandoned.

[51] Int. Cl.[6] .............................. G06K 9/00; G06K 9/40; A61N 5/00; A61N 6/00

[52] U.S. Cl. .......................... 382/131; 128/922; 128/925; 250/492.2; 378/7; 378/901; 382/275

[58] Field of Search .................................... 382/128, 131, 382/132, 263, 275; 378/4, 7, 901; 128/920, 922, 923; 250/492.2

[56] References Cited

U.S. PATENT DOCUMENTS

| | | | |
|---|---|---|---|
| 4,858,128 | 8/1989 | Nowak | 382/131 |
| 4,897,788 | 1/1990 | King | 378/4 |
| 4,994,965 | 2/1991 | Crawford et al. | 64/413.15 |
| 5,046,003 | 9/1991 | Crawford | 364/413.15 |
| 5,165,100 | 11/1992 | Hsieh et al. | 382/131 |
| 5,170,346 | 12/1992 | Crawford et al. | 364/413.16 |
| 5,212,737 | 5/1993 | Ackelsberg | 382/131 |
| 5,225,980 | 7/1993 | Hsieh et al. | 364/413.13 |
| 5,251,128 | 10/1993 | Crawford | 364/413.13 |
| 5,271,055 | 12/1993 | Hsieh et al. | 378/4 |
| 5,287,276 | 2/1994 | Crawford et al. | 364/413.14 |
| 5,297,036 | 3/1994 | Grimaud | 364/413.13 |
| 5,301,108 | 4/1994 | Hsieh | 364/413.19 |
| 5,473,656 | 12/1995 | Hsieh et al. | 378/4 |

*Primary Examiner*—Bipin Shalwala
*Attorney, Agent, or Firm*—John S. Beulik; John H. Pilarski

[57] ABSTRACT

The present invention, in one form, corrects any error due to varying z-axis detector cell gains represented in data obtained by a scan in a CT system. In accordance with one form of the present invention, and after correcting the image data for beam-hardening, the data is passed through a highpass filter to remove any data representing relatively slow, or low frequency, changes. Next, the filtered data is clipped and view averaged to remove high frequency data contents due to the objects being imaged. A slope estimate is then created. Using the slope estimate, an error estimate is generated. The error estimate is then subtracted from the beam-hardened corrected data, for example. As a result, errors due to z-axis gain variation of the detector cells are removed from the projection data array.

13 Claims, 5 Drawing Sheets

DETECTOR Z-AXIS GAIN CORRECTION FOR A CT SYSTEM

This application is a continuation of application Ser. No. 08/376,813 filed Jan. 23, 1995 now abandoned.

FIELD OF THE INVENTION

This invention relates generally to computed tomography (CT) imaging and more particularly, to correcting image data for any error introduced into such data due to combining the output signals of x-ray detector cells having different individual gains.

BACKGROUND OF THE INVENTION

In CT systems, an x-ray source projects a fan-shaped beam which is collimated to lie within an X-Y plane of a Cartesian coordinate system, termed the "imaging plane". The x-ray beam passes through the object being imaged, such as a patient, and impinges upon a linear array of radiation detectors. The intensity of the transmitted radiation is dependent upon the attenuation of the x-ray beam by the object. Each detector of the linear array produces a separate electrical signal that is a measurement of the beam attenuation. The attenuation measurements from all the detectors are acquired separately to produce a transmission profile.

The x-ray source and the linear detector array in a CT system are rotated with a gantry within the imaging plane and around the object so that the angle at which the x-ray beam intersects the object constantly changes. A group of x-ray attenuation measurements from the detector array at one gantry angle is referred to as a "view". A "scan" of the object comprises a set of views made at different gantry angles during one revolution of the x-ray source and detector. In an axial scan, data is processed to construct an image that corresponds to a two dimensional slice taken through the object. One method for reconstructing an image from a set of data is referred to in the art as the filtered back projection technique. This process converts the attenuation measurements from a scan into integers called "CT numbers" or "Hounsfield units", which are used to control the brightness of a corresponding pixel on a cathode ray tube display.

Detectors utilized in CT systems include detectors generally known as 2-D detectors. With such 2-D detectors, a plurality of detector cells form separate columns and the columns are arranged in rows. In a CT system having such a 2-D detector, sometimes referred to as a multislice system, the intensity of detector measurements are derived by combining, along the z direction. multiple detector outputs. These outputs are supplied as inputs to a data acquisition system. If the detector outputs to be combined are obtained from detectors having different individual gains, the combined signal represents a weighted sum of the incoming detector signals where the different detector gains cause different weighting. The error introduced by detector gain differences is object-dependent and cannot be removed by a standard gain calibration. Therefore, in order to more accurately create an image from such data, there exists a need to provide a manner for correcting the image data in view such error.

SUMMARY OF THE INVENTION

The present invention, in one form, corrects the error in projection data resulting from the combination of the data from x-ray detector cells having different individual gains. More particularly, the present algorithm estimates the error due to combining the data from x-ray detector cells having different individual gains. The estimated error is subtracted from the projection data thereby removing such error from the projection data.

In accordance with one form of the present invention, and after correcting data from the x-ray detector cells for beam-hardening, the data is passed through a highpass filter to remove any data representing relatively slow, i.e. low frequency, changes. High pass filtering provides a "rough" separation of the error data from the true signal data.

The error data is then clipped and "view averaged" to remove high frequency data contents which are true signal data. Particularly, some actual data from the image to be reconstructed has a high frequency and should be filtered out. Clipping and view averaging removes the high frequency object data while maintaining the error data due to the detector gain variation.

Based on the clipped and "view averaged" estimate, intensity slope estimates along the z-direction are generated. An error estimate based on such slope estimates is then determined. Such error estimate then is subtracted from the beam-hardening corrected data to remove the error data from the projection data. In this manner, errors due to z-axis gain variation of the detector cells is corrected.

DETAILED DESCRIPTION OF THE DRAWINGS

Figure 1:
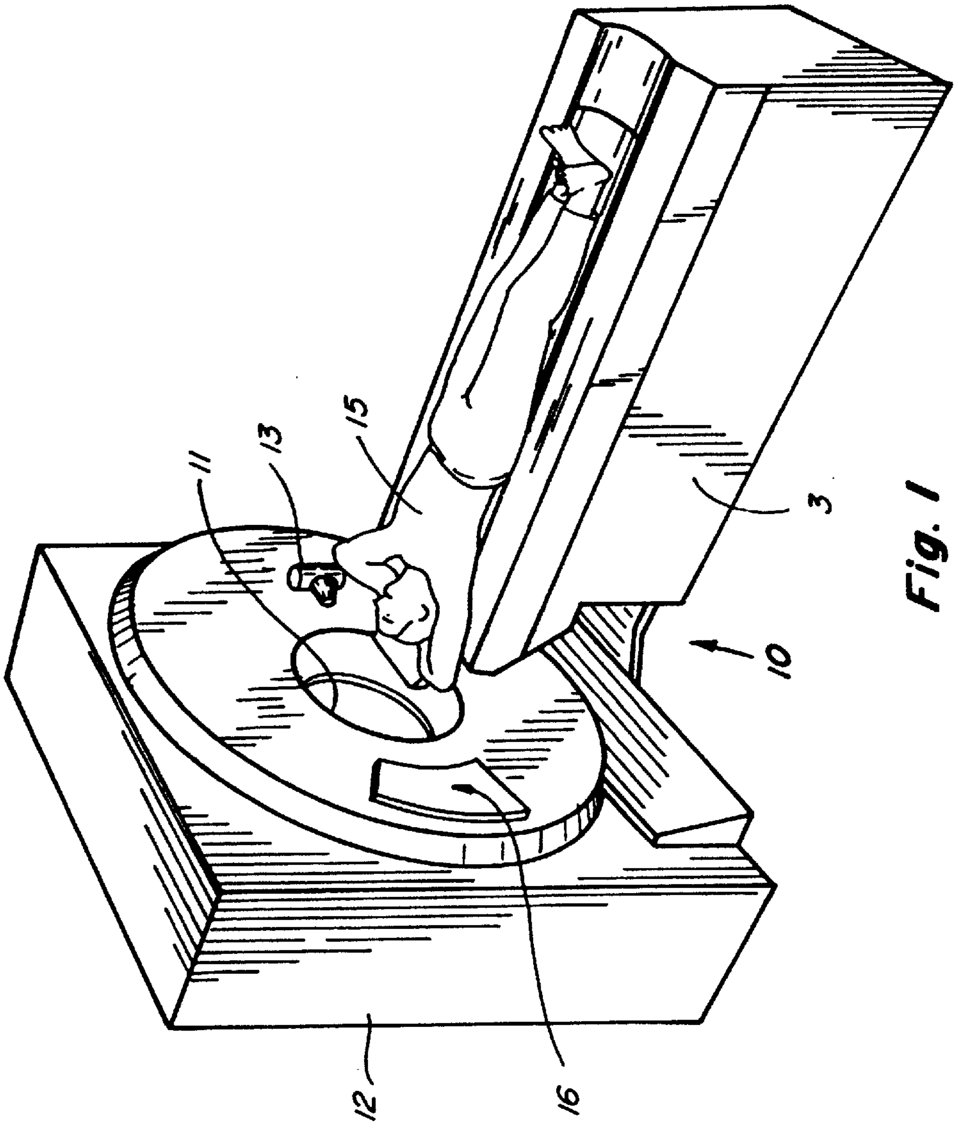
FIG. 1 is a pictorial view of a CT imaging system in which the present invention may be employed.
Figure 2:
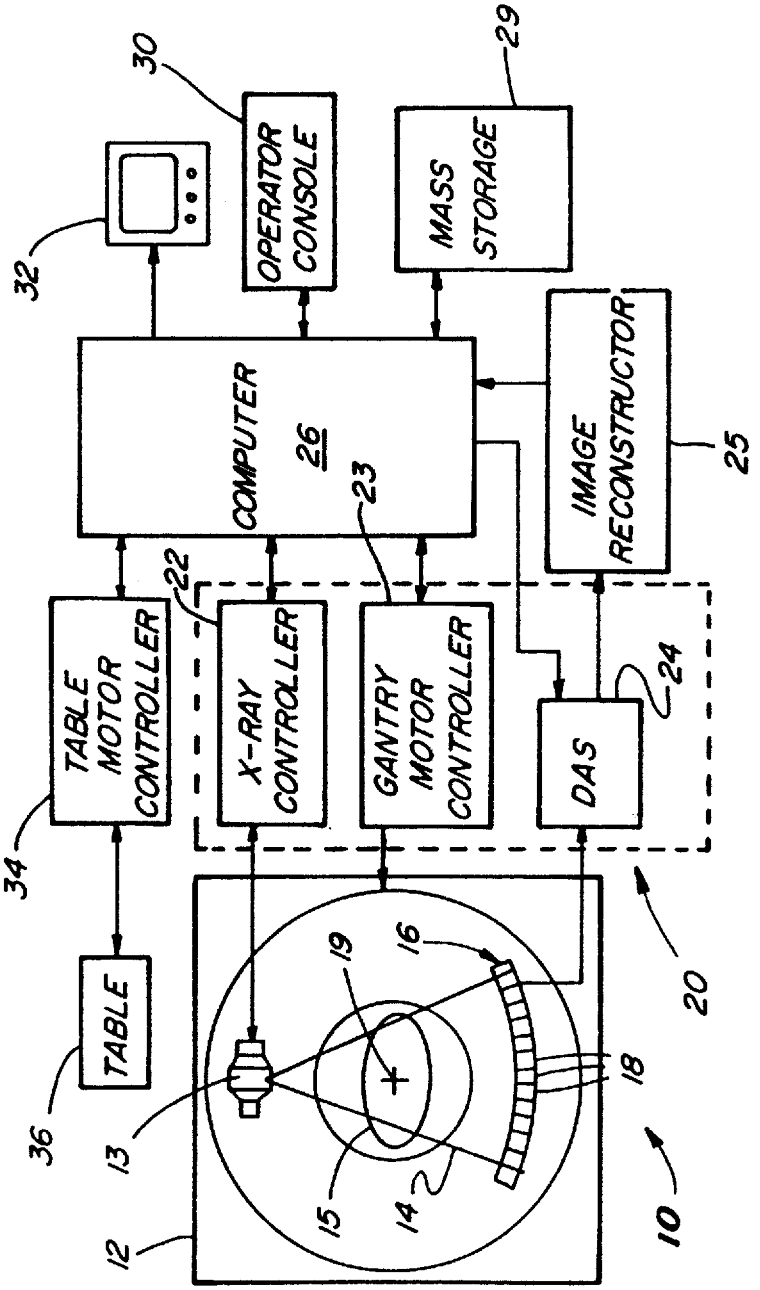
FIG. 2 is a block schematic diagram of the CT imaging system illustrated in FIG. 1.

With reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of gantry 12. Detector array 16 is formed by two rows of detector elements 18 which together sense the projected x-rays that pass through a medical patient 15. Each detector element 18 produces an electrical signal that represents the intensity of an impinging x-ray beam and hence the attenuation of the beam as it passes through patient 15. During a scan to acquire x-ray projection data, gantry 12 and the components mounted thereon rotate about a center of rotation 19.

Rotation of gantry 12 and the operation of x-ray source 13 are governed by a control mechanism 20 of CT system 10. Control mechanism 20 includes an x-ray controller 22 that provides power and timing signals to x-ray source 13 and a gantry motor controller 23 that controls the rotational speed and position of gantry 12. A data acquisition system (DAS) 24 in control mechanism 20 samples analog data from detector elements 18 and converts the data to digital signals for subsequent processing. An image reconstructor 25 receives sampled and digitized x-ray data from DAS 24 and performs high speed image reconstruction. The reconstructed image is applied as an input to a computer 26 which stores the image in a mass storage device 29.

Computer 26 also receives commands and scanning parameters from an operator via console 30 that has a keyboard. An associated cathode ray tube display 32 allows the operator to observe the reconstructed image and other data from computer 26. The operator supplied commands and parameters are used by computer 26 to provide control signals and information to DAS 24, x-ray controller 22 and gantry motor controller 23. In addition, computer 26 operates a table motor controller 34 which controls a motorized table 36 to position patient 15 in gantry 12.

Figure 3:
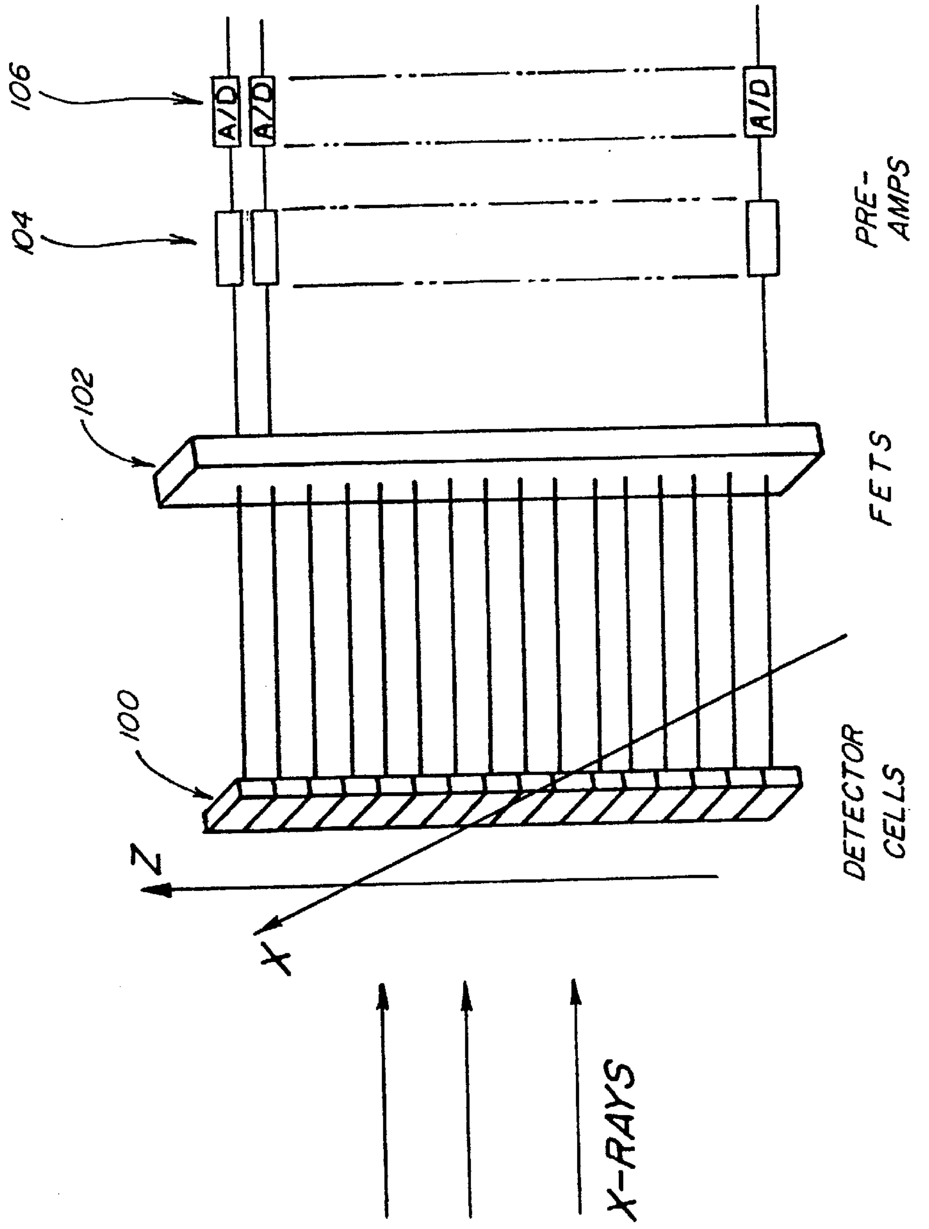
FIG. 3 is a block diagram depiction of a column of detector cells of a detector and related controls.

FIG. 3 illustrates a column of detector cells 100 coupled to a switches (e.g. field effect transisters (FETs) 102. Detector column 100 is composed of a plurality of detector cells arranged in a column. Although not shown, a complete detector is composed of a plurality of detector columns forming rows of detector cells along the z-axis. As explained above, each detector cell produces an electrical signal that represents the intensity of an impinging x-ray beam and hence the attenuation of the beam as it passes through a patient. The output of each cell is supplied through FETs 102 to preamplifiers 104 which supply an amplified signal to an analog-to-digital converters 106. The digitized signal is then supplied to computer 26 for further processing and image reconstruction.

In operation FETs 102 controls supply of output signals from each detector cell row to the pre-amplifiers 104. For example, FETs 102 are "opened" and "closed" under the control of switch control assembly (not shown). When a particular FET is closed, the output signal from the corresponding detector cell is provided to pre-amp 104. When the FET is open, no signal is provided by such cell to pre-amp 104.

FETs 102 may enable one or more than one detector cell during a particular sample time. For example, one detector cell in a column may be enabled during each sample time. Two cells also may be enabled during each sample time. Pre-amps 104 provide an amplified output of such signals to A/D converters 106.

Figure 4:
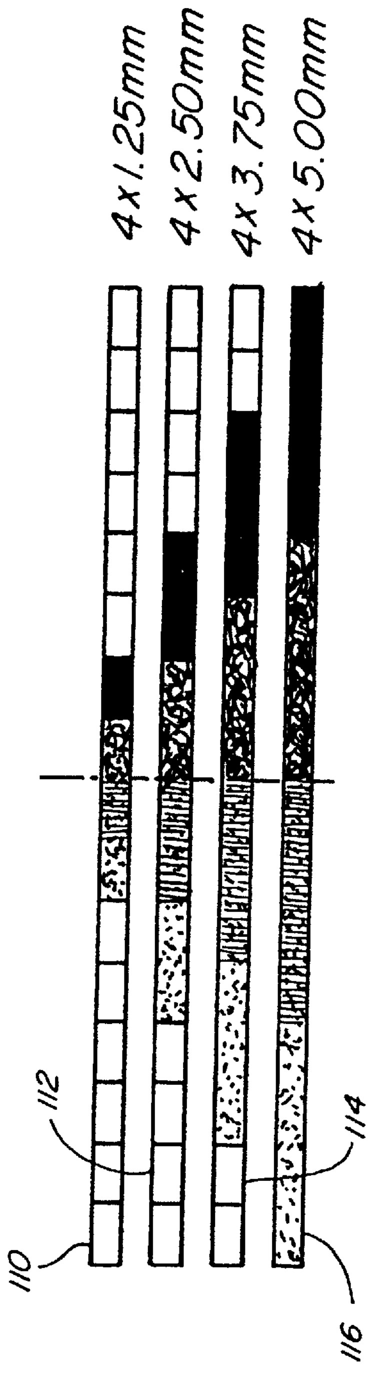
FIG. 4 illustrates detector cell data combining for various thickness image slices.

The number of cells activated in each channel during each sample time is determined by the slice dimensions of the image desired to be reconstructed. For example, as shown in FIG. 4, sixteen detector cells are arranged in a column. Although shown horizontally in FIG. 4, it should be understood that the cells in FIG. 4 correspond to the column shown in FIG. 3. The top column 110 corresponds to the cell outputs for an image slice that is 4×1.25 mm in size. The bottom column 116 corresponds to the cell combinations for an image slice that is 4×5.00 mm in size.

With a thin slice (e.g., a 4×1.25 mm slice), no summing of detector cells is performed. For a thicker slice (e.g., a 4×2.50 mm slice), detector cell summing is performed. As shown in FIG. 4, for the 4×2.50 mm slice, two cells are summed as shown in column 2 (112) as indicated by shading. For the 4×3.75 mm slice (column 3(116)), three cells are summed and for the 4×5.00 mm slice (column 4(118)), four cells are summed. Such summing is performed w hen reconstructing images for thicker slices since for thicker slices, adequate coverage can be obtained and processing time can be reduced by summing the detector cell outputs as set forth above.

When summing detector cell outputs, an error is introduced into the summed signal due to the fact that each detector cell has a different gain. When the detector cell outputs are summed, the error due to the different gains is included in the resulting signal (e.g., the digitized signal output by A/D converter 106). The present algorithm corrects the projection data for any errors resulting from combining signals from detector cells having different gains.

More particularly, data provided to computer 26 (FIG. 2) typically first is preprocessed (by computer 26) to correct for various well-known errors such as beam-hardening. The present correction algorithm could be implemented to form a part of such preprocessing after beam-hardening correction but before PCAL correction, as illustrated in FIG. 5.

Figure 5:
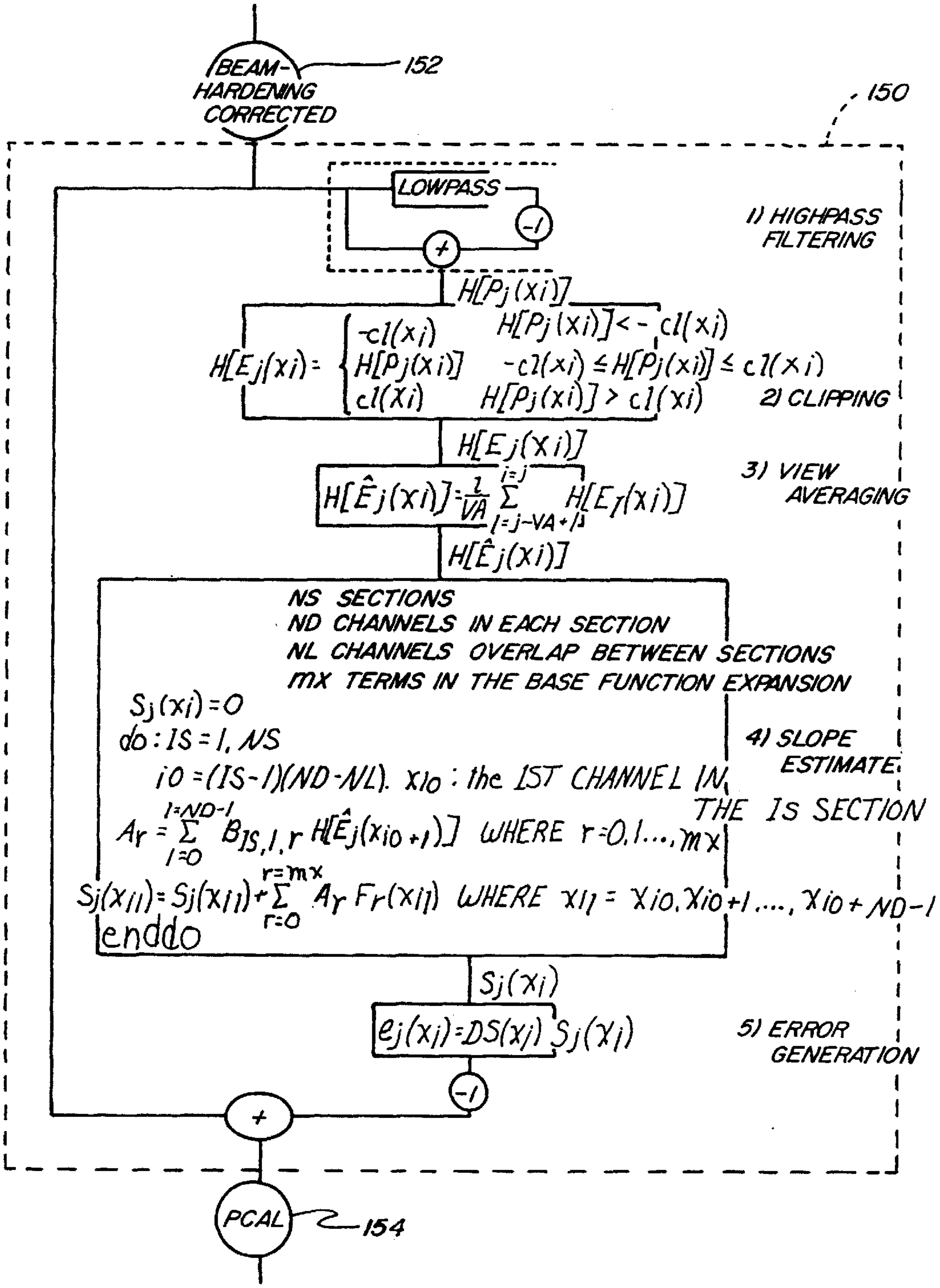
FIG. 5 is a flow chart illustrating a sequence of process steps in accordance with one form of the present invention.

Referring to the flow chart illustrated in FIG. 5, assume that four detectors are combined in the z direction to define a 5 mm slice. The number of detectors combined, of course, may vary and could be less than or greater than four (e.g., the number of detectors combined could be generally represented by the designation "nz"). The number of detectors combined for the following explanation is selected for illustrative purposes only and is not a limitation or requirement of the present algorithm. With respect to the example of combining the outputs of four detectors, the four detectors to be combined have individual gains $g_k$ where k=1, 2, 3, 4. The x-ray intensity seen by each individual detector is $I_k$ where k=1, 2, 3, 4. The measured data, denoted as Y, can be modeled as follows:

$$Y=\sum_{k=1}^{k=4} g_k I_k. \tag{1}$$

Gain normalization occurs as a consequence of air normalization. The gain-normalized data $I_m$ is give by:

$$I_m = Y/G = \sum_{k=1}^{k=4} g_k/G \cdot I_k, \tag{2}$$

where G is the average gain of the combined module to be considered, i.e.:

$$G = 1/4 \sum_{k=1}^{k=4} g_k. \tag{3}$$

The measurement desired to be obtained, denoted as I, is:

$$\tilde{I} = \sum_{k=1}^{k=4} I_k. \tag{4}$$

The gain of each individual detector can be expressed as:

$$g_k = G + \delta g_k, \tag{5}$$

where $\delta g_k$ is the remaining part of $g_k$. The physical meaning of $\delta g_k$ is the gain variation of the detectors. Using equation 5 with equation 2, factorizing G and recalling equation 4 provides:

$$I_m = \sum_{k=1}^{k=4} I_k + \sum_{k=1}^{k=4} (\delta g_k/G(I_k)) = \tilde{I} + \sum_{k=1}^{k=4} (\delta g_k/G) I_k. \tag{6}$$

Equation 6 relates the true signal, I, the signal derived from the measured data, $I_m$, and the error due to the detector z-axis gain variation.

Given that log (1+x)≈x and $I_m$≈I, equation 6 can be rewritten as follows:

$$-\log(I) \approx -\log(\tilde{I}_m) + \Delta E, \tag{7a}$$

where $$\Delta E = \sum_{k=1}^{k=4} (\delta g_k/G)(I_k/\tilde{I}). \tag{7b}$$

If the z profile of the incoming x-ray flux, $I_k$, is known, equations 7*a* and 7*b* can be used to remove the z-axis error. Estimating $I_k$ adequately is important in accurately removing such error.

Equation 7*b* holds for every data point. Thus, there are a total of (NxxNz) equations, where Nx and Nz represent the number of data samples per view along the fan beam direction (the x direction) and along the direction perpendicular to the fan beam (the z direction), respectively. Although all these equations can be used simultaneously, in accordance with one form of the present algorithm, only the data from the same detector row (the same z location) are coupled to solve the simultaneous equations. Particularly, i denotes the x index (the channel Index), where i=1, 2, . . . n. This results in n equations:

$$\Delta E(x_i) = \sum_{k=1}^{k=4} ((\delta g(x_i, z_i)/G(x_i))(I(x_i, z_i)/\tilde{I}(x_i)) \tag{8}$$

where $i = 1, \ldots, n$

An accurate and stable solution can be achieved by a high pass version of equation 8. A linear highpass operator, H[f(x)], can be defined as:

$$H[f(x)] = f(x) - \text{Lowpass}\,[f(x)], \tag{9}$$

where Lowpass [f(x)] is a low-passed version of f(x). As an example, several points boxcar average can be used. Applying this operator to equation 8 provides:

$$H[\Delta E(x_i)] \approx \sum_{k=1}^{k=4} H[(\delta g(x_i, z_i)/G(x_i))][I(x_i, z_i)/\tilde{I}(x_i)], \tag{10}$$

where $i = 1, \ldots, n$

In equation 10, it is assumed that the part of $I(x_i, z_i)/\bar{I}(x_i)$ that causes the z-axis problem changes relatively slowly in the x direction, and therefore, can be factored out from the highpass operator. Equation 10 provides a mathematical foundation for matching the detector "finger prints", as defined by the high-passed gains, with the error term.

Over a certain region, $I(x_i, z,)/\bar{I}(x_i)$ can be further approximated by some low-frequency base functions. As an example, the following is provided by using a power series expansion:

$$I(x, z)/\tilde{I}(x) \approx \sum_{iz=1}^{iz=mz} c_{iz}(x) z^{iz} \approx c_1(x) z. \tag{11}$$

The $c_0(x_i)$ term has no contribution to the z-axis correction, and therefore, is ignored. Also, only the linear term with respect to z is retained in the second part of equation 11. Under the assumption of a slope term only in z, equation 10 can be rewritten as:

$$H[\Delta E(x_i)] \approx H[(3(g_4(x_i) - g_1(x_i)) + (g_3(x_i) - g_2(x_i)))/G(x_i)] c_1(x_i) \Delta z. \tag{12}$$

Since the error term depends only on gain variations, an erroneous slope estimate does not contribute an error term to those channels which have no gain variations.

The function $c_1(x_i)$ can be further expanded as follows:

$$c_1(x) \approx \sum_{ix=0}^{ix=mx} c_{ix} x^{ix}. \tag{13}$$

The corresponding coefficients can be determined by solving equations 10 or 12 in the least squares sense.

Although in equation 10 or 12 H[ΔE(x)] is unknown, it can be estimated. As an example, a value can be approximated by the corresponding highpass version of the projection data $P(x_i)$, i.e., H[ΔE(x)]≈H[P(x)], as suggested by equation 7*a*. H[P(x)] not only contains the errors due to the detector gain variation, but also contains high frequencies that belong to the object being imaged. To obtain robust and stable corrections, an estimation of H[ΔE(x)] that minimizes the high frequency contents from the object while maintaining the errors due to the detector gain variation should be used.

The following two techniques can be used to improve the H[ΔE(x)]estimation:

1) $c_M$ denotes the maximal value of $c_1(x_i)$ in clinical applications. It then follows from equations 10 and 11 that:

$$|H[\Delta E(x_i)]| \leq c_M f(x_i) \quad i = 1, \ldots, n \tag{14a}$$

where $$f(x_i) = \left| \sum_{k=1}^{k=4} H[\delta g(x_i, z_k)/G(x_i)]\, z_k \right|. \tag{14b}$$

$f(x_i)$ is a function of the detector gain characteristics only and can be pre-calculated. Thus, the H[ΔE(x)] estimation that does not satisfy equation 14 can be clipped as follows:

$$H[\Delta E(x_i)] = \begin{cases} -c_M f(x_i) & H[P(x_i) < -c_M f(x_i) \\ H[P(x_i)] & -c_M f(x_i) \leq H[P(x_i)] \leq c_M f(x_i) \\ c_M f(x_i) & H[P(x_i)] > c_M f(x_i) \end{cases} \tag{15}$$

2) The H[ΔE(x)] estimation derived from equation 15 can be averaged across views to further suppress the high frequency contents that belong to the object being imaged.

With the improved estimation of H[ΔE(x)], the corresponding coefficients in equation 13 can be determined in the least squares sense. The base function expansion works well for fitting a small region. When the fitting region is large, it can be subdivided into sub-regions and fitted separately. Some feathering can be applied to assure a smooth transition between sub-regions.

The closeness of this fitting can be evaluated by computing the correlation coefficients, denoted as r. h(r) denotes the closeness index, where 0≦h(r)≦1. The higher the value of h(r), the closer the fitting. Thus, the final estimate of $I(x_i,z_k)/\bar{I}(x_i)$ can be expressed in one of following ways:

$$I(x, z)/\tilde{I}(x) \approx z \sum_{ix=0}^{ix=mz} c_{ix} x^{ix}, \tag{16a}$$

$$I(x, z)/\tilde{I}(x) \approx h(r) z \sum_{ix=0}^{ix=mx} c_{ix} x^{ix}, \tag{16b}$$

$$I(x, z)/\tilde{I}(x) \approx h(r) z \sum_{ix=0}^{ix=mx} c_{ix} x^{ix} + (1 - h(r)) z S. \tag{16c}$$

where S is an estimate of $I(X_i,z_k)/\bar{I}(x_i)$ derived by other known methods. Once the function $I(x_i,z_k)/\hat{I}(x_i)$ is determined, equations 7*a* and 7*b* can be used to remove the z-axis error.

To reduce the implementation burden, it might be sufficient to update the $I(x_i,z_k)/\bar{I}(x_i)$ estimation once every several views. The interval for updating the stimulation can be determined by experiment.

Referring now specifically to FIG. 5, one form of the present correction algorithm is outlined in the dashed box

150. As set forth in FIG. 5, the algorithm can be applied after beam hardening correction 152 but before the PCAL correction 154 and includes the following five steps: 1) high-pass filtering, 2) clipping, 3) view averaging, 4) slope estimate, and 5) error generation. In FIG. 5, the j and i indexes represent the view and channel indexes.

The first step of high pass filtering is described in equation 9. The second step of clipping is described in equation 15, where the ceiling function $cl(x_i)$is described in equation 14. View averaging is shown as the third step in FIG. 5.

The fourth step of generating a slope estimate is an important step in the present algorithm. The NC center channels where the correction is to be applied are subdivided into NS sections, with ND channels in each section and NL channels overlap between adjacent sections. The slope is estimated section by section. $x_{io}$ denotes the first channel in the Isth section. mx+1 is the number of terms retained in equation 13. For the Isth section, a (mx+1)×ND matrix, $(b_{is,r,l})$, is defined as follows:

$$b_{is,r,l} = f(x_{io+l})\ (l - 0.5ND)^r \text{ for } \quad (17a)$$

$$l = 0, \ldots, ND-1 \text{ and}$$

$$r = 0, \ldots, mx$$

$$\text{where } f(x = \sum_{k=1}^{k=nz} H[\delta g(x,z_k)/G(x)]z_k. \quad (17b)$$

$(B_{is,l,r})$ denotes the inverse matrix of$(b_{is,l,r})$. $(B_{is,l,r})$ is a ND×(mx+1) matrix. Furthermore, functions $F_r(x_{io+l})$ are defined as follows:

$$F_r(x_l)=K(x_l-x_o)\ (l-0.5ND)^r \text{ for } l=0,\ldots,ND-1 \text{ and } r=0,\ldots,mx \quad (18)$$

where, $K(x_l-x_o)$ is a feathering function to assure a smooth transition from section to section. An example of the feathering function is given as follows:

$$K(x) = \begin{cases} 0 & x \leqq 0 \\ 3\,(x/NL)^2 - 2\,(x/NL)^3 & 0 < x < NL \\ 1 & NL \leqq x \leqq ND - NL \\ 3\,(ND - x/NL)^2 - 2\,(ND - x/NL)^3 & ND - NL < x < ND - 1 \\ 0 & x \geqq ND - 1 \end{cases} \quad (19)$$

With $(B_{is,l,r})$ and $F_r(x_l)$ defined as above, the fourth step can be carried out as illustrated in FIG. 5.

The detector Z-slope sensitivity function, DS(s), is defined as follows:

$$DS(x) = \sum_{k=1}^{k=nz} (\delta g(x,z_k)/G(x))z_k \quad (20)$$

Therefore, the fifth step of error generation can be performed as shown in FIG. 5.

The ceiling function $cl(x_i)$, the slope estimate matrix $(B_{is,l,r})$ and the detector Z-slope sensitivity $DS(x_i)$ depend on detector characteristic and the slice thickness only, and therefore can be pre-calculated during the detector gain determination. $F_r(x_l)$ is determined by the parameters ND and NL and mx, and can also be pre-calculated.

Example parameters of the algorithm illustrated in FIG. 4 are listed below.

NC: Number of channels to be corrected (650);

NS: Number of sections (14);

ND: Number of channels in each section (60);

NL: Number of overlapping channels between sections (15); mx and mz: Number of terms in the base function expansion (5,1);

VA: Number of views to be averaged (0,15);

NV: Number of views between two adjacent error updates (0);

FS: Hp filter size (3);

$C_M$: Factor for the ceiling function.

From the preceding description of several embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. The present invention, however, may be used with many other CT systems including "fourth generation" systems wherein the detector is a full-ring stationary detector and only the x-ray source rotates with the gantry. The present invention could also be utilized in connection with stop-and-shoot as well as helical scanning type CT systems. Moreover, although the present invention, in one form, has been described being performed on data subsequent to beam-hardening correction, the present invention could be implemented at various points in the data correction/processing. Accordingly, the spirit and scope of the invention are to be limited only by the terms of the appended claims.

What is claimed is:

1. A system for producing a tomographic image of an object, said system comprising a detector having a plurality of detector cells having known individual gains, said system configured to spatially integrate individual cell signals and to sum the spatially integrated individual cell signals, the number of cells whose output signals are summed based upon a selected slice thickness, and to correct the summed signal for gain errors resulting from summing output signals from a plurality of cells having different individual gains by:

(a) high pass filtering the summed signal;

(b) clipping the high-passed filtered signal;

(c) view averaging the filtered and clipped signal;

(d) creating a slope estimate based on the filtered, clipped, and view-averaged signal; and (e) identifying the error using the slope estimate.

2. A system in accordance with claim 1 wherein the detector cell gain error correction is performed subsequent to performing a beam-hardening correction.

3. A system in accordance with claim 1 wherein high-pass filtering the data comprises performing the steps of:

(a) identifying the low frequency components of the projection data; and (b) summing the negative value of the low frequency components with the projection data.

4. A system in accordance with claim 1 wherein clipping the high-pass filtered data is performed in accordance with the following function:

$$H[\Delta E(x_i)] = \begin{cases} -c_M f(x_i) & H[P(x_i)] < -c_M f(x_i) \\ H[P(x_i)] & -c_M f(x_i) \leqq H[P(x_i)] \leqq c_M f(x_i) \\ c_M f(x_i) & H[P(x_i)] > c_M f(x_i), \end{cases}$$

5. A system for producing a tomographic image of an object, said system comprising a detector having a plurality of detector cells having known individual gains, said system being configured to spatially integrate individual cell signals and to sum the spatially integrated individual cell signals, the number of cells whose output signals are summed based upon a selected slice thickness, and to correct the summed signal for any error resulting from summing output signals from a plurality of cells having different individual gains.

6. A system in accordance with claim 5 wherein the detector cell gain error correction is performed subsequent to performing a beam-hardening correction.

7. A system in accordance with claim 5 wherein said system comprises a data acquisition system which corrects the projection data for any error resulting from different individual gains of said cells by:

(a) high pass filtering the data;

(b) clipping the high-passed filtered data;

(c) view averaging the clipped data;

(d) creating a slope estimate based on the view-averaged data; and (e) identifying the error data using the slope estimate.

8. A system in accordance with claim 7 wherein high-pass filtering the data comprises performing the steps of:

(a) identifying the low frequency components of the projection data; and (b) summing the negative value of the low frequency components with the projection data.

9. A system in accordance with claim 7 wherein clipping the high-pass filtered data is performed in accordance with the following function:

$$H[\Delta E(x_i)] = \begin{matrix} -c_M f(x_i) & H[P(x_i)] < -c_M f(x_i) \\ H[P(x_i)] & -c_M f(x_i) \leqq H[P(x_i)] \leqq c_M f(x_i) \\ -c_M f(x_i) & H[P(x_i)] > c_M f(x_i) \end{matrix}$$

10. A method for correcting a summed signal generated by spatially integrating individual cell signals and summing the spatially integrated individual cell signals from a plurality of detector cells of a detector in an imaging system for detector cell gain error, the detector cells having known different individual gains, said method comprising the steps of:

(a) high pass filtering the summed signal;

(b) clipping the high-passed filtered summed signal;

(c) view averaging the filtered and clipped summed signal;

(d) creating a slope estimate based on the filtered, clipped, and view-averaged summed signal; and (e) identifying the error using the slope estimate.

11. A method in accordance with claim 10 wherein the detector cell gain error correction is performed subsequent to performing a beam-hardening correction.

12. A method in accordance with claim 10 wherein high-pass filtering the data comprises performing the steps of:

(a) identifying the low frequency components of the projection data; and (b) summing the negative value of the low frequency components with the projection data.

13. A method in accordance with claim 10 wherein clipping the high-pass filtered data is performed in accordance with the following function:

$$H[\Delta E(x_i)] = \begin{cases} -c_M f(x_i) & H[P(x_i)] < -c_M f(x_i) \\ H[P(x_i)] & -c_M f(x_i) \leqq H[P(x_i)] \leqq c_M f(x_i) \\ c_M f(x_i) & H[P(x_i)] > c_M f(x_i). \end{cases}$$

* * * * *